(12) United States Patent
Kondo

(10) Patent No.: US 7,706,500 B2
(45) Date of Patent: Apr. 27, 2010

(54) X-RAY CT APPARATUS

(75) Inventor: Gen Kondo, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 102 days.

(21) Appl. No.: 12/170,798

(22) Filed: Jul. 10, 2008

(65) Prior Publication Data

US 2009/0022267 A1   Jan. 22, 2009

(30) Foreign Application Priority Data

Jul. 18, 2007  (JP) .............................. 2007-186793

(51) Int. Cl.
  *A61B 6/03* (2006.01)
  *G21K 1/04* (2006.01)

(52) U.S. Cl. .................... 378/15; 378/150; 378/151; 378/152

(58) Field of Classification Search .............. 378/15, 378/150, 151, 152
See application file for complete search history.

(56) References Cited

U.S. PATENT DOCUMENTS

| | | | | |
|---|---|---|---|---|
| 6,907,100 B2 * | 6/2005 | Taguchi | .................... | 378/4 |
| 6,990,170 B2 * | 1/2006 | Sugihara et al. | ................ | 378/15 |
| 7,106,824 B2 * | 9/2006 | Kazama et al. | ................ | 378/16 |
| 7,113,569 B2 * | 9/2006 | Okumura et al. | ............. | 378/150 |
| 7,313,216 B2 * | 12/2007 | Nishide et al. | ................. | 378/15 |
| 7,409,034 B2 * | 8/2008 | Gohno | ......................... | 378/7 |
| 7,508,903 B2 * | 3/2009 | Nishide et al. | ................. | 378/15 |
| 7,522,697 B2 * | 4/2009 | Satta et al. | .................... | 378/15 |

FOREIGN PATENT DOCUMENTS

| | | |
|---|---|---|
| JP | 10-248835 | 9/1998 |
| JP | 2001-145621 | 5/2001 |
| JP | 2002-17716 | 1/2002 |
| JP | 2006-51233 | 2/2006 |

* cited by examiner

*Primary Examiner*—Allen C. Ho
(74) *Attorney, Agent, or Firm*—Oblon, Spivak, McClelland, Maier & Neustadt, L.L.P.

(57) ABSTRACT

The supporter supports a patient and is disposed movably along the body axis direction of said patient. The imaging part includes an X-ray-generator and an X-ray-detector. The X-ray-generator irradiates X-rays while rotating around the body axis. The X-ray-detector detects the X-rays that have permeated the patient. The collimator changes the irradiation field of the X-rays to be irradiated. The scan controller controls the movement of the supporter and the imaging part. The image-reconstructing part reconstructs image data based on the X-rays that have been detected by the X-ray detector. The movement amount-detector detects the amount of movement of the patient by the supporter. The collimator controller controls so as to change the size of the opening of the collimator based on the amount of movement.

7 Claims, 5 Drawing Sheets

X-RAY CT APPARATUS

BACKGROUND OF THE INVENTION

1. Field of the Invention

The present invention relates to an X-ray CT apparatus that controls a collimator for restricting the irradiation field of X-rays (or X-ray beam).

2. Description of the Related Art

X-ray computed tomography apparatuses are known by which X-rays are irradiated at a patient and image data is reconstructed from the permeation data. An X-ray computed tomography apparatus for multi-slicing makes it possible to collect data regarding a plurality of slices from different positions all together at a time by using an X-ray detector in which detecting elements (e.g., an assembly of a scintillator and photo diode) for detecting X-rays are arranged in a row. The combined use of multi-slice scanning (also referred to as cone-beam scanning) and helical scanning makes it possible to collect data of an extremely wide scanning range within a short time, so propagation in the future is anticipated.

One important objective in the case of the combined use of multi-slice scanning and helical scanning is the reduction of exposure to radiation dose. For example, there is technology in which a scanning range is set so as to include the region of a subjected organ on a scanogram and the opening of a collimator is set in accordance with the scanning range so that the scanning is restricted to the subjected organ within the patient (e.g., Japanese Unexamined Patent Application Publication No. 2002-17716 and Japanese Unexamined Patent Application Publication No. H10-248835). However, in reality, a part of the targeted organ is left out from the scanning range, resulting in missing data. Therefore, a situation may occur in which rescanning becomes necessary.

In this respect, it is possible to reconstruct a scanned image even if the data is missing, but in reality, noise ends up being inserted into the portion of the reconstructed scanned image where the data was missing. In addition, when a doctor uses the scanned image as a reference for diagnosis, the area of the diagnosis such as cancer is extremely small. Therefore, it is difficult to distinguish the difference of the noise that has been inserted into the scanned image from a diseased site, so there is a risk of misdiagnosis. For this reason, it is necessary to reduce the amount of exposure to radiation without missing data.

Accordingly, technology has been proposed in the past for reducing the radiation exposure of a patient at the time of helical scanning by changing the opening degree (size of the irradiation field) of the opening of a collimator in accordance with the position on a body axis in the progressing course of the helical scanning (e.g., Japanese Unexamined Patent Application Publication No. 2006-51233).

However, with the conventional method of changing the opening degree of the opening of a collimator, only the coordinate of the direction of movement of the bed of the collimator opening is acquired, and the opening degree of the opening of the collimator is preliminarily determined with respect to said coordinate. Thus, it is difficult to say that the timing of data collection via a data collection system corresponds to the control of the opening of the collimator, the data collection system including an imaging part such as an X-ray irradiator or an X-ray detector. Therefore, correlation of the collected data and the opening degree of the collimator is unclear, and there is a risk of missing data or of subjecting a patient to excessive radiation exposure.

Furthermore, in recent years, technology referred to as variable speed helical scanning has been proposed, whereby scanning is performed by changing the speed of movement in the body axis direction and the helical pitch while collecting data of a designated scanning range. In this respect, the collimator is simply controlled according to the distance by which the bed is moved, so with the conventional method of collimator control, it has been difficult to control the opening of the collimator with favorable accuracy with respect to the changes of the speed of movement or the helical pitch in such variable speed helical scanning.

SUMMARY OF THE INVENTION

The purpose of the present invention is to provide an X-ray CT apparatus for conducting quantitative collimator control on the basis of a data collection system by synchronizing with the timing pulse of the data collection system and changing the size of the opening of the collimator.

According to a first aspect of the present invention, the X-ray CT apparatus comprises the following functioning parts. A supporter supports a patient and is disposed movably along the body axis direction of said patient. An imaging part includes an X-ray-generator and an X-ray-detector. The X-ray-generator irradiates X-rays while rotating around the body axis. The X-ray-detector detects the X-rays that have permeated a patient. A collimator changes the irradiation field of X-rays to be irradiated. A scan controller controls the movement of the supporter and the imaging part. An image-constructing part reconstructs image data based on the X-rays that have been detected by the X-ray detector. A detector detects the amount of movement of a patient by the supporter. A collimator controller controls so as to change the size of the opening of a collimator based on the amount of movement.

According to the first aspect, with this constitution, the quantitative control of the opening of a collimator is conducted by synchronizing with the timing pulse based on a starting signal of the data collection system including the imaging part such as an X-ray-generator or an X-ray-detector and then changing the size of the opening of the collimator based on the number of pulses. Therefore, the operation timing of the data collection system and the opening/closing of the collimator may accurately be matched, and it is possible to reduce the portion of the region that is subjected to excessive radiation exposure, but it is not used for the reconstruction, while preventing data from being missing. Furthermore, it becomes possible to control the opening of the collimator with favorably accuracy in accordance with the scanning range, even during variable speed helical scanning.

DETAILED DESCRIPTION OF THE EMBODIMENTS

Embodiment 1

Figure 1:
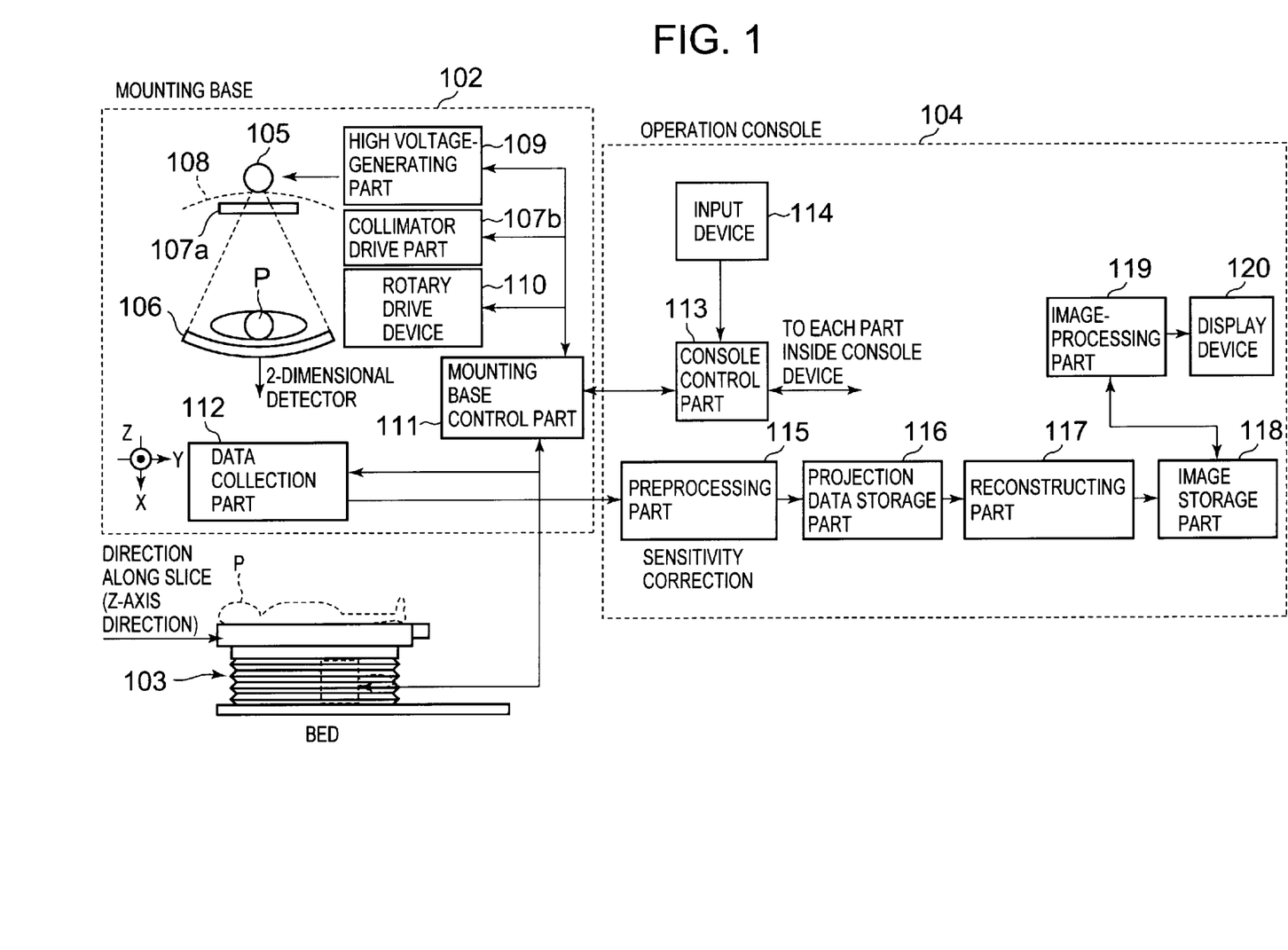
FIG. 1 is a schematic diagram representing the constitution of the hardware of the X-ray CT apparatus according to the present invention.

Hereinafter, an embodiment of the present invention will be described. FIG. 1 is a diagram representing the hardware constitution of the X-ray CT apparatus according to the present embodiment. The X-ray CT apparatus comprises: a mounting base 102 constituted for collecting projection data regarding a patient P, a bed 103 for moving the patient P thereon, and an operation console 104 for performing entry and image display for operating the X-ray CT apparatus.

The mounting base 102 has an X-ray tube 105, X-ray detector 106, collimator plate 107a, collimator drive part 107b, rotary frame 108, high voltage-generating part 109, rotary drive device 110, mounting base control part 111, and data collection part 112. The X-ray tube 105 and X-ray detector 106 are attached to the rotary frame 108. With this constitution, rotation of the rotary frame 108 by the rotary drive device 110 enables rotation around the patient P while the X-ray tube 105 and X-ray detector 106 are opposing each other. Herein, the X-ray tube 105 is equivalent to the "X-ray-generating part" in the present invention.

The X-ray tube 105 generates X-rays in accordance with tube voltage that is supplied from the high voltage-generating part 109. The X-ray detector 106 is a two-dimensional array type detector (also referred to as a multi-slice type detector). An X-ray detecting element has, for example, a square-shaped detecting surface of 0.5 mm×0.5 mm. For example, 916 X-ray detecting elements are arranged in the channel direction and, for example, more than 64 rows are arranged in parallel along the slicing direction (direction of the rows of the detector).

An X-ray diaphragm device is constituted of a collimator plate 107a and a collimator drive device 107b. The X-ray diaphragm device is for adjusting the irradiation range in the slicing direction of the X-rays to be irradiated at a patient. The collimator drive device 107b moves the collimator plate 107a to change the X-ray irradiation range in the slicing direction.

In general, the data collection part 112, referred to as a DAS (data acquisition system), amplifies signals that are output from the detector 106 for each channel and converts the same to digital signals. The projection data (raw data) is supplied to the operation console 104 external to the mounting base.

The mounting base control part 111 controls the high voltage-generating part 109, collimator drive device 107b, rotary drive device 110, data collection part 112, etc., based on the control signal from a console control part 113.

The bed 103 comprises a top plate on which to place a patient and a top plate drive device for moving the top plate along the slicing direction. The center portion of the rotary frame 108 has an opening, and a patient P that has been placed on the top plate, is introduced into the opening. It should be noted that the direction parallel to the rotating center axis of the rotary frame 108 is defined as the Z-axial direction (slicing direction), and the plane perpendicularly crossing it in the Z-axial direction is defined as the X-axial direction and Y-axial direction.

The operation console 104 comprises: a console control part 113, input device 114, preprocessing part 115, projection data storage part 116, reconstructing part 117, image storage part 118, image-processing part 119, and display device 120.

The reconstructing part 117 uses projection data that has been stored in the projection data storage part 116 and reconstructs images of information regarding the live body of a patient. This reconstruction may be performed by methods: of fan-beam reconstruction in which the passage of X-rays is presumed to be parallel in the slicing direction; and of cone-beam reconstruction in which the X-ray irradiation angle (cone angle) in the slicing direction is taken into consideration.

The image storage part 118 stores the reconstructed images. The image-processing part 119 generates a display image by performing various types of image processing on the image data that has been stored in the image storage part 118. Setting various types of setting conditions, regions of interest, or the like, in the event of generating a display image, is performed based on entry into the input device 114 by the operator. The display device 120 displays the image that has been generated by the image-processing part 119. Furthermore, the console control part 113 is configured to send a control signal to the mounting base control part 111 so that scanning such as helical scanning is performed based on entry by the operator. It should be noted that the operation console 104 may be constituted of a proprietary hardware, or the same function may also be realized by software using a computer.

Figure 2:
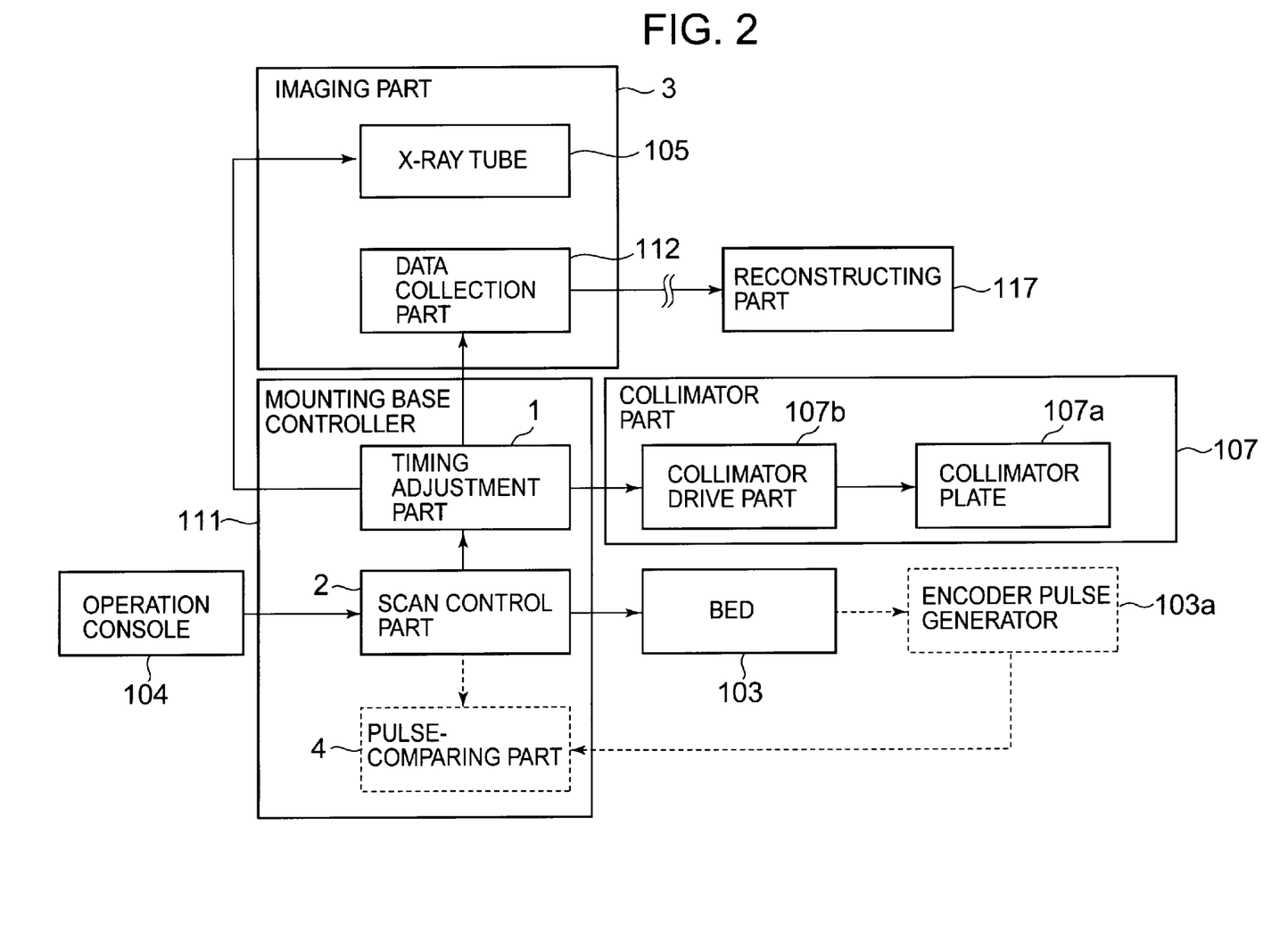
FIG. 2 is a block diagram representing the function of the X-ray CT apparatus according to the present invention.

Next, the collimator control of the X-ray CT apparatus according to the present embodiment is described in detail with reference to FIG. 2. FIG. 2 is a block diagram representing the function of the X-ray CT apparatus according to the present invention. The bed 103 in FIG. 2 is equivalent to the "supporting part" in the present invention, the X-ray tube 105 to the "X-ray-generating part" in the present invention, and the data collection part 112 to the "X-ray-detector" in the present invention. The mounting base control part 111 is constituted of a timing adjustment part 1 and a scan control part 2. Herein, the timing adjustment part 1 sends signals for operating the collimator drive part 107 by synchronizing with the operation of the imaging part 3 and is equivalent to the "detector" in the present invention. The scan control part 2 is configured to send the same pulse signals to the imaging part 3 and the bed 103 so that the two are synchronized and operated. Furthermore, the collimator part 107b is constituted of a collimator drive part 107b and a collimator plate 107a. The collimator plate 107a is equivalent to the "collimator" in the present invention. Moreover, the collimator drive part 107b is equivalent to the "collimator control part" in the present invention. Herein, the mounting base control part 111, collimator drive part 107b, and image-constructing part 117 each comprise a CPU (Central Processing Unit).

Figure 3:
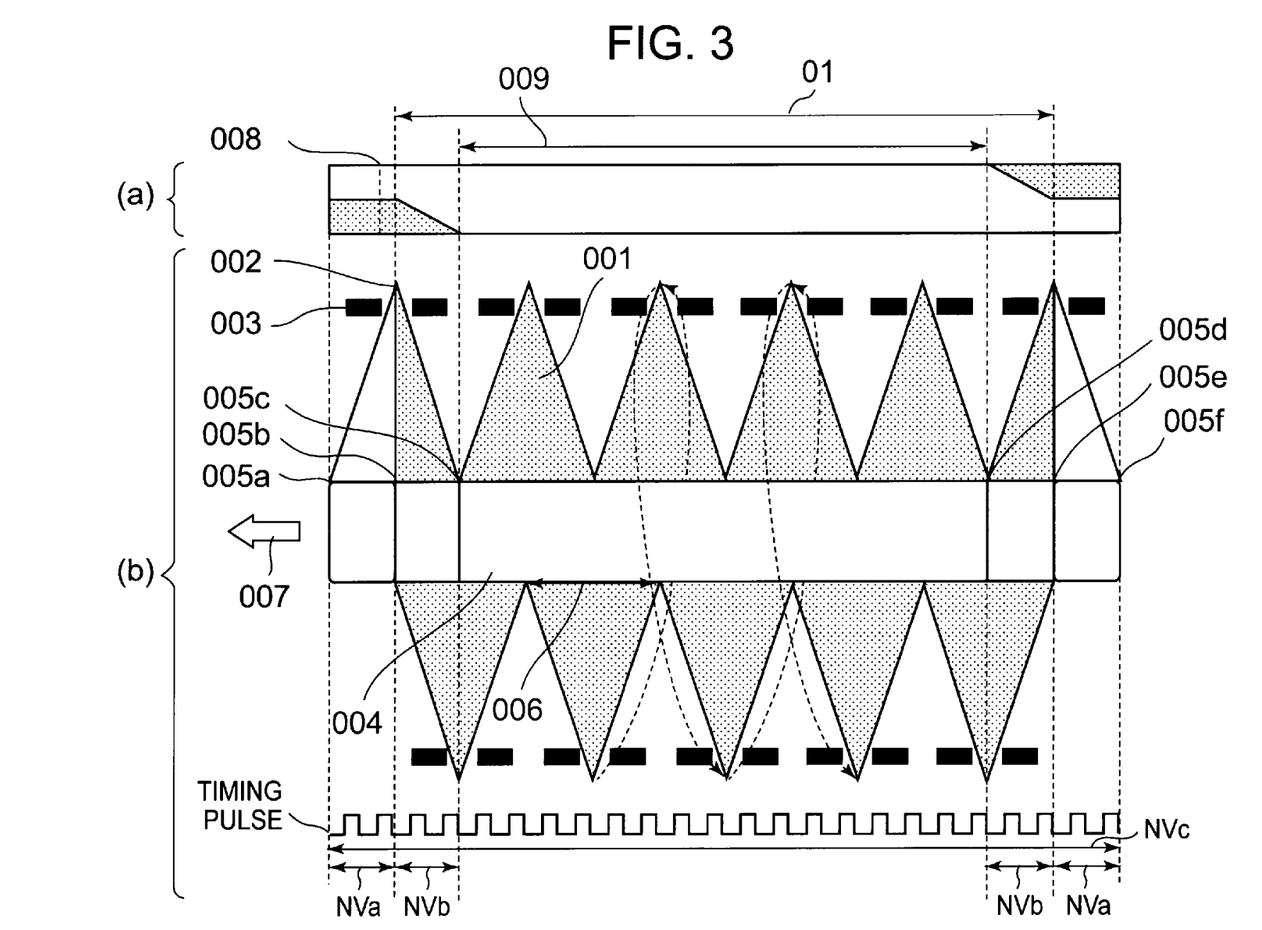
FIG. 3 is a figure for explaining X-ray irradiation of a patient and the corresponding process of operations of the opening of a collimator.

FIG. 3 is a figure for explaining X-ray irradiation of a patient by the X-ray CT apparatus according to the present invention and the corresponding process of operations of the opening of a collimator 003 (the collimator 003 is equivalent to the collimator plate 107a in FIG. 2). The collimator 003 in the present embodiment is constituted of movable blades on the left and right, and thus, the opening is semi-closed, and the blades are arranged so that one each on the left and right is independently movable. The irradiation field of X-rays is restricted by the movement of the blades. FIG. 3(b) is a drawing in which the state of a patient 004 on the bed 103 is viewed from above. The bed 103 moves in the direction of a direction of movement 007. In this respect, the bed 103 is moved in the direction of movement 007 for imaging, but for convenience, FIG. 3 is a figure in which the bed 103 is fixed, while the imaging part 3 is moved along with the passage of time. Each triangle 001 shows X-ray irradiation from an X-ray-generating source 002. FIG. 3 shows a state in which the X-ray-generating source 002 as well as the data collection part 112 (not illustrated in FIG. 3) have moved toward the right of the figure along with the movement of the patient 004 toward the left of the figure. Furthermore, the X-ray-generating source 002 as well as the data collection part 112 are rotating in vertically with respect to the body axis of the patient 004. Herein, the irradiation field of the X-ray irradiated from the X-ray-generating source 002 is restricted by the blades of the collimator 003. The irradiated X-ray is made incident to the patient 004 in the range of an irradiation range 006. Furthermore, the range from point 005$a$ to point 005$f$ represents a position along the body axis of the patient 004. Point 005$a$ is the starting position of the X-ray irradiation; point 005$b$ is the foremost position of an imaging region 010 that is required for reconstructing an image of a region of interest 009; point 005$c$ is the foremost position of the region of interest 009; point 005$d$ is the end position of the region of interest 009; point 005$e$ is the end position of the imaging region 010; and point 005$f$ is the end position of the X-ray irradiation. Furthermore, FIG. 3($a$) shows the degree of opening (size of the irradiation field) of the collimator 003 corresponding to the position of movement of the X-ray-generating source 002 and the data collection part 112. For example, position 008, taken as a reference, represents the state in which the opening of the collimator 003 is semi-closed at the position. Herein, the degree of opening of the collimator 003 is controlled via movement of the blades of the opening of the collimator 003.

Herein, the regions from point 005$a$ to point 005$b$ and from point 005$e$ to 005$f$ are regions where X-ray is irradiated on half of the surface of the detector. Furthermore, the region from point 005$b$ to point 005$c$ is a region where the irradiation field becomes wider as the opening of the collimator 003 gradually opens, and the region from point 005$d$ to point 005$e$ is a region where the irradiation field becomes narrower as the opening of the collimator 003 gradually closes.

Operators like a doctor or an operation engineer (hereinafter simply referred to as "operator") uses the operation console 104 and designates an image-generating range (or scanning range) on the scanogram. That is, the region of interest 009 from point 005$c$ to point 005$b$ shown in FIG. 3 is designated. The mounting base control part 111 automatically ascertains point 005$a$, point 005$b$, point 005$e$, and point 005$f$ shown in FIG. 3 based on the entered reconstructing conditions such as the slicing thickness, and sends the position of each point to the scan control part 2.

Herein, in the present embodiment, the engineer enters two points corresponding to the region of interest 009 to ascertain the position of each point, but there is no particular limit for this as long as the five distances corresponding to the interval of each of the points is discovered. For example, with this constitution, an engineer may enter all of the distances, and it is also possible to enter some of the distances so that the remaining distances are obtained from other conditions.

The scan control part 2 converts each entered distance to: a sequential number of pulses NVc from the starting position of the X-ray irradiation (point 005$a$) to the end position of the X-ray irradiation (point 005$f$); number of pulses NVa from the starting position of the X-ray irradiation (point 005$a$) to the forefront of the imaging region 008 (point 005$b$); and number of pulses NVb from the forefront of an imaging region 010 (point 005$b$) to the forefront of the region of interest 009 (point 005$c$). Herein, number of pulses NVa and number of pulses NVb are sequential, and number of pulses NVa and number of pulses NVb are part of the sequential number of pulses NVc. Furthermore, as for the number of pulses corresponding to the distance, for example, if the cycle of one pulse is T and the speed of movement of the bed 103 is v, the distance that the bed 103 moved during one pulse is represented as vT, so the number of pulses corresponding to the distance L is calculated by L/vT.

Next, the scan control part 2 starts to move the bed 103. Based on the speed of movement of the bed 103 and the distance from the start position of moving the bed 103 (not illustrated) to the start position of X-ray irradiation (point 005$a$) (hereinafter, referred to as "operation start distance), the scan control part 2 calculates the number of pulses corresponding to the operation starting distance (from the start of moving the bed 103 until the X-ray irradiation is started by the X-ray tube 105). Furthermore, the scan control part 2 generates a timing pulse for driving the imaging part 3 and sends, to the timing adjustment part 1, number of pulses NVc, number of pulses NVb, number of pulses NVa, the number of pulses corresponding to the operation start distance, and the timing pulse.

In the present embodiment, number of pulses NVa is the number of pulses of the first segment and the number of pulses of the fifth division. Number of pulses NVb is the number of pulses of the second division and the number of pulses of the fourth division. Subtraction of the two folds of the number of pluses NVa and number of pulses NVb from number of pulses NVc is equivalent to the number of pulses of the third division. Herein, according to the present embodiment, the distance from point 005$a$ to point 005$b$ is the same as the distance from point 005$e$ to 005$f$, so the number of pulses thereof is regarded as NVa. Moreover, the distance from point 005$b$ to point 005$c$ is the same as the distance from point 005$d$ to point 005$e$, so the number of pulses thereof is regarded as NVb. If these distances differ, the different number of pulses may be adapted. Furthermore, the starting position of the X-ray irradiation (point 005$a$) to the end position of the X-ray irradiation (point 005$f$) is clear, so the number of pulses equivalent to the distance is regarded as the number of pulses NVc. But whichever distance is used for the number of pulses is not particularly limited as long as all five distances that have been entered beforehand are represented by the number of pulses to be calculated herein. As for the number of pulses, for example, number of pulses NVc may also be the number of pulses from point 005$c$ to point 005$d$.

The timing adjustment part 1 receives, from the scan control part 2, the number of pulses that corresponds to the operation start distance, counts the timing pulse, and sends, to the X-ray tube 105, a signal for initiating the X-ray irradiation (hereinafter simply referred to as "starting signal") when the count reaches the number of pulses that corresponds to the operation starting distance. The position for sending the starting signal is point 005$a$.

Moreover, the timing adjustment part 1 counts the timing pulse after the starting signal is sent at point 005$a$, sends a signal for starting detection to the data collection part 112 when the count reaches number of pulses NVa, and sends, to the collimator drive part 107$b$, a signal to initiate full opening of the opening of the collimator plate 107$a$. Furthermore, number of pulses NVb is sent to the collimator drive part 107$b$. The position for sending the signal to start detection and the signal to start full opening of the opening is point 005$b$.

Subsequently, once the count of the timing pulse since the starting signal is sent reaches the addition of number of pulses NVa and number of pulses NVb, the timing adjustment part 1 sends a signal to the collimator drive part 107$a$ for maintaining a fully opened state. Point 005$c$ is the position for sending the signal for maintaining a fully opened state.

Subsequently, once the count of the operation reference pulse since the starting signal is sent reaches a number that is obtained by subtracting number of pulses NVa and number of pulses NVb from number of pulses NVc, the timing adjustment part 1 sends, to the collimator drive part 107b, a signal to start closing of the opening of the collimator plate 107a. Moreover, number of pulses NVb is sent to the collimator drive part 107b. Point 005d is the position for sending the signal to start closing.

Subsequently, once the count of the timing pulse since the starting signal is sent reaches a number that is obtained by subtracting number of pulses NVa from number of pulses NVc, the timing adjustment part 1 sends, to the collimator drive part 107b, a signal for maintaining a semi-open state. Furthermore, the timing adjustment part 1 sends a signal to an X-ray detection device 112 for detecting the end. Point 005e is the position for sending the signal to stop operation and the signal to end detection.

Subsequently, once the count of the operation reference pulse since the starting signal is sent reaches number of pulses NVc, the timing adjustment part 1 sends, to the x-ray tube 105, a signal for ending the X-ray irradiation (hereinafter, simply referred to as "ending signal"). Point 005f is the position for sending the ending signal.

The X-ray tube 105 receives the starting signal at point 005a and starts the irradiation of X-rays. Furthermore, the X-ray tube 105 receives the ending signal at point 005f and ends the irradiation of X-rays.

The data collection part 112 receives the signal to start detection at point 005a and starts the detection of X-ray data. Furthermore, the data collection part 112 receives the signal to end detection at the 005f and ends the detection of X-ray data. The data collection part 112 repeats the detection of X-ray data after receiving the signal to start detection until the signal to end detection is received. Herein, the detection of X-ray data means that X-rays are read out in accordance with the timing pulse by the data collection parts 112 that have been arranged in a row.

Herein, according to the present embodiment, the data collection system including the imaging part 3 and the control of the opening of the collimator plate 107a are synchronized by the timing pulse. The synchronization also includes a case in which the phase is the same but the cycle is in integral multiples, (e.g., the first pulse is an integral multiple of the second pulse, or the second pulse is an integral multiple of the first pulse), in addition to the case in which the pulse (first pulse) for controlling the detection of X-ray data and the pulse (second pulse) for controlling the opening of the collimator plate 107a are exactly in the same cycle and the same phase. Alternatively, the case is included in which the cycle is same and the phase is displaced for certain amount.

Once movement of the bed 103 is started by the scan control part 2, the collimator drive part 107b moves the blade on the side of the direction of movement 007 of the bed 103 (cf. FIG. 3) to realize a semi-open state by closing half of the opening of the collimator plate 107a on the side of the direction of movement 007 of the bed 103. Thereby, as shown in FIG. 3, the blade is to be maintained in a state in which the opening of the collimator plate 107a is semi-closed on the side of the direction of movement 007 of the bed 103, during the period from point 005a (which is the starting position of the X-ray irradiation) to point 005b.

After receiving the signal to start full opening from the timing adjustment part 1, the collimator drive part 107b starts moving the blade on the side of the direction of movement 007 of the bed 103 (cf. FIG. 3) to fully open the opening of the collimator plate 107a. Then, the collimator drive part 107b receives number of pulses NVb, calculates the speed of movement of the blade so as to be fully opened after the duration of number of pulses NVb, and moves the blade at that speed. Thereby, the movement of the blade starts from point 005b in FIG. 3, and the opening reaches a fully open state at point 005c.

Next, the collimator drive part 107b receives the signal from the timing adjustment part 1 for maintaining a fully open state and maintains the blade in a state in which the opening of the collimator plate 107a is fully open during the period from point 005c to point 005d.

Next, the collimator drive part 107b receives the signal from the timing adjustment part 1 to start closing and starts moving the blade on the side that is opposite the direction of movement 007 of the bed 103 (cf. FIG. 3), because the side opposite to the direction of movement 007 of the bed 103 of the opening of the collimator plate 107a is semi-closed at point 005d. Then, the collimator drive part 107b receives number of pulses NVb, calculates the speed of movement of the blade so that the opening of the collimator plate 107a becomes semi-closed after a duration of number of pulses NVb, and moves the blade at the speed. Thereby, the movement of the blade from point 005d in FIG. 3 starts and the side of the direction of movement of the bed 103 of the opening of the collimator plate 107a comes to a semi-closed state at point 005e.

Next, the collimator drive part 107b receives the signal for maintaining semi-open state from the timing adjustment part 1 and maintains the blade in a state in which the side is semi-closed that is opposite to the direction of movement 007 of the bed 103 of the opening of the collimator plate 107a during the period from point 005e to point 005f.

In the starting portion of the scanning shown in FIG. 3, the projection data of the portion from 005a to 005b (a portion of 005e to the 005f in the ending portion) is not used for the reconstruction of images. Therefore, as described above, it becomes possible to reduce the radiation exposure of the patient by controlling the collimator plate 107a so as not to irradiate X-rays to the patient 004 in that portion.

Figure 4:
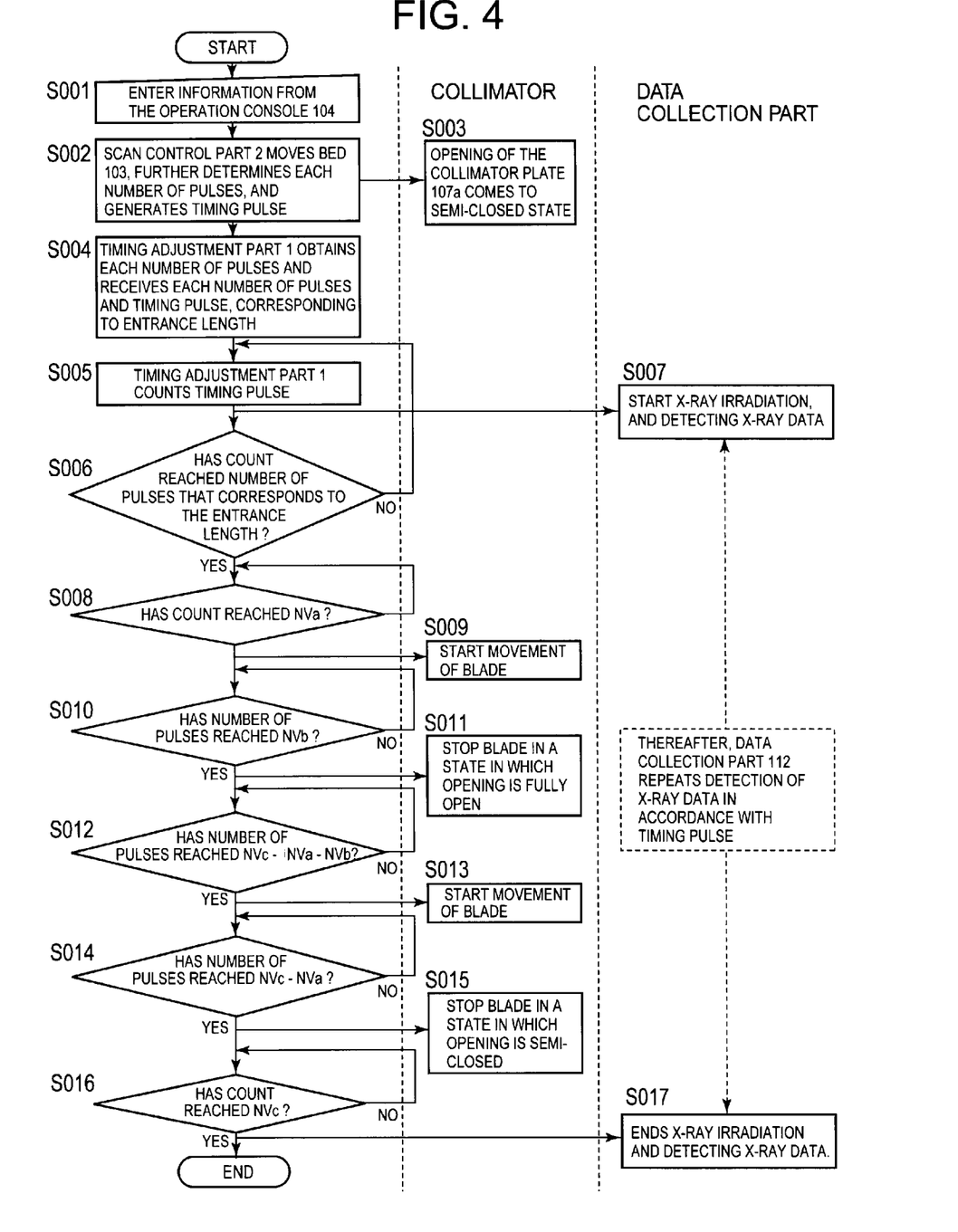
FIG. 4 is a flowchart showing the flow of operations of the X-ray CT apparatus according to the present invention.

Next, with reference to FIG. 4, data collection by X-ray irradiation and the corresponding flow of operations of the opening of the collimator plate 107a according to the present embodiment will be described. FIG. 4 is a flowchart showing the operations of the X-ray CT apparatus according to the present embodiment. In the flowchart, the left side divided by the dotted lines is primarily the flow of timing control, the center thereof divided by the dotted lines is the flow of operations of the collimator plate 107a, and the right side divided by the dotted lines is a flowchart showing the flow of operations of the X-ray tube 105 and the data collection part 112.

Step S001: An engineer enters information such as information regarding positions, direction of movement 007 of the bed 103, irradiation range 006, and the like, from the operation console 104.

Step S002: The scan control part 2 receives the information from the operation console 104, starts moving the bed 103, generates a timing pulse, and further obtains, from information of each position and the timing pulse, number of pulses NVa, number of pulses NVb, number of pulses NVc, and the number of pulses corresponding to the entrance length.

Step S003: The collimator drive part 107b moves the blade so that the side of the direction of movement 007 of the bed 103 of the opening of the collimator plate 107a comes to a semi-closed state.

Step S004: The timing adjustment part 1 receives, from the scan control part 2, number of pulses NVa, number of pulses NVb, number of pulses NVc, the number of pulses corresponding to the entrance length, and the timing pulse.

Step S005: The timing adjustment part 1 counts the timing pulse. Hereinafter, the timing adjustment part 1 continues to count the timing pulse until the end.

Step S006: The timing adjustment part 1 determines whether or not the count of the timing pulse has reached the number of pulses that corresponds to the entrance length. If not reached, the counting of the timing pulse is repeated, and if reached, the timing adjustment part 1 sends a starting signal to the X-ray generating part 105 and proceeds to Step S008.

Step S007: On receipt of the starting signal from the timing adjustment part 1, the X-ray-irradiating part 105 starts X-ray irradiation, and the data collection part 112 starts detecting X-ray data. Thereafter, the data collection part 112 repeats the detection of the X-ray data until a signal to end detection is received from the timing adjustment part 1 in step S017.

Step S008: The timing adjustment part 1 determines whether or not the count of the timing pulse has reached number of pulses NVa. If not reached, the counting of the timing pulse is repeated, and if reached, the timing adjustment part 1 sends a signal to start detection to the data collection part 112, sends a signal to start full opening for the collimator plate 107a to the collimator drive part 107b, and proceeds to step S010.

Step S009: The collimator drive part 107b receives the signal to start full opening from the timing adjustment part 1, and starts opening the blade on the side of the direction of movement 007 of the bed 103 at the opening of the collimator plate 107a.

Step S010: The timing adjustment part 1 determines whether or not the count of the timing pulse has reached number of pulses NVb. If not reached, the counting of the timing pulse is repeated, and if reached, the timing adjustment part 1 sends a signal of operation stop to the collimator drive part 107b and proceeds to step S012.

Step S011: The collimator drive part 107b receives a signal of maintaining full opening from the timing adjustment part 1 and maintains the blade in a state in which the opening of the collimator plate 107a is fully open.

Step S012: The timing adjustment part 1 determines whether the count of the timing pulse has reached the number of pulses that is obtained by subtracting number of pulses NVa and number of pulses NVb from number of pulses NVc. If not reached, the counting of the timing pulse is repeated, and if reached, the timing adjustment part 1 sends, to the collimator drive part 107b, a signal to start closing for the opening of the collimator plate 107a, and proceeds to step S014.

Step S013: The collimator drive part 107b receives the signal to start closing from the timing adjustment part 1 and starts closing the blade that is on the opposite side to the direction of movement 007 of the bed 103 at the opening of the collimator plate 107a.

Step S014: The timing adjustment part 1 determines whether the count of the timing pulse has reached the number of pulses that is obtained by subtracting number of pulses NVa from number of pulses NVc. If not reached, the counting of the timing pulse is repeated, if reached, the timing adjustment part 1 sends a signal of operation stop to the collimator drive part 107b, sends a signal to end detection to the data collection part 112, and proceeds to step S016.

Step S015: The collimator drive part 107b receives a signal of maintaining semi-opening from the timing adjustment part 1 and maintains the blade in a state in which the opposite side to the direction of movement 007 of the bed 103 of the opening of the collimator plate 107a is semi-closed.

Step S016: The timing adjustment part 1 determines whether or not the count of the timing pulse has reaches number of pulses NVc. If not reached, the counting of the timing pulse is repeated, and if reached, an ending signal is sent to the X-ray tube 105.

Step S017: The X-ray tube 105 receives the ending signal from the timing adjustment part 1 and ends the X-ray irradiation. The data collection part 112 receives a signal to end detection from the timing adjustment part 1 and ends detecting the x-ray data.

As described above, unlike the conventional control of the degree of opening of the collimator plate 107a which was being conducted, e.g. based on the position on the body axis of the X-ray-generating part with respect to a patient, as for the control of the opening of the collimator plate 107a according to the present embodiment, the control is conducted by synchronizing with the pulse of a signal for driving the data collection system including the imaging part 3 using a starting signal. Thereby, it becomes possible to quantitatively control the degree of opening of the collimator plate 107a (size of the irradiation field), and unnecessary radiation exposure with respect to the patient may be reduced.

Furthermore, in recent years, among technologies for capturing X-ray CT images by returning to a region of interest, there has been technology for imaging while accelerating/decelerating within the region of interest to maintain the continuity of images (such technology is sometimes referred to as "shuttle helical"). In the case of shuttle helical imaging, if a collimator plate is simply controlled based on the generated timing pulse as in the past, because the control for the accelerated/decelerated portion becomes complicated, there is a risk of deterioration of the repeatability of the operation of the collimator plate with respect to the operation of a mounting base. On the contrary to this, in the X-ray CT apparatus according to the present embodiment, because even in the event of imaging by shuttle helical, the collimator plate is controlled by the position of the bed, the control becomes easier, thus, making it possible to enhance the repeatability of the operation of the collimator plate for the operation in objective.

Embodiment 2

The X-ray CT apparatus according to the present embodiment is configured so as to issue a warning, in the X-ray CT apparatus according to the first embodiment, in the case when the synchronization of the operation of the bed 103 and the operation of the control of the data collection system including the imaging part 3 as well as the collimator plate 107a becomes insufficient. Hereinafter, the determination is described regarding whether the operation of the bed 103 and the operation of the control of the data collection system including the imaging part 3 as well as the collimator plate 107a are synchronized insufficiently or not, and the warning issue thereof is also described.

As shown by the dotted line in FIG. 2, in addition to the X-ray CT apparatus in the first embodiment, the X-ray CT apparatus according to the present embodiment further comprises an encoder pulse-generating part 103a that is attached to the bed 103 and a pulse-comparing part 4.

The bed 103 is moved by the pulse signal that is sent by the scan control part 2. Herein, because the pulse signal is the same pulse as the timing pulse for driving the imaging part 3 or the collimator plate 107a, the operation of the control of the data collection system including the imaging part 3 as well as the collimator plate 107a and the operation of the bed 103 are supposed to be synchronized.

However, due to the load of the motor for driving the bed 103, etc., in reality, there is a risk that the operation of the bed 103 will not be completely synchronized with the pulse signal that is being sent. Therefore, the encoder pulse-generating part 103a is attached to the bed 103 and the encoder pulse-generating part 103a generates a pulse in accordance with the actual moved distance of the bed 103 (hereinafter, referred to as "support base encoder pulse").

The pulse-comparing part 4 receives an encoder pulse and a timing pulse.

The pulse-comparing part 4 divides the frequency of the timing pulse for the timing pulse so as to have the same clock as the encoder pulse. Herein, the frequency of the timing pulse is divided in order to make the control simpler, but it is also possible to adjust the clock by multiplying the encoder pulse.

By comparing the timing pulse and the encoder pulse in which the clocks have been adjusted, a warning is issued in the case of having a difference that exceeds a permissible preliminarily set value for the pulse cycle. The notice of the warning is issued, e.g., by displaying it in a display part (not illustrated) or by sounding an alert.

Figure 5:
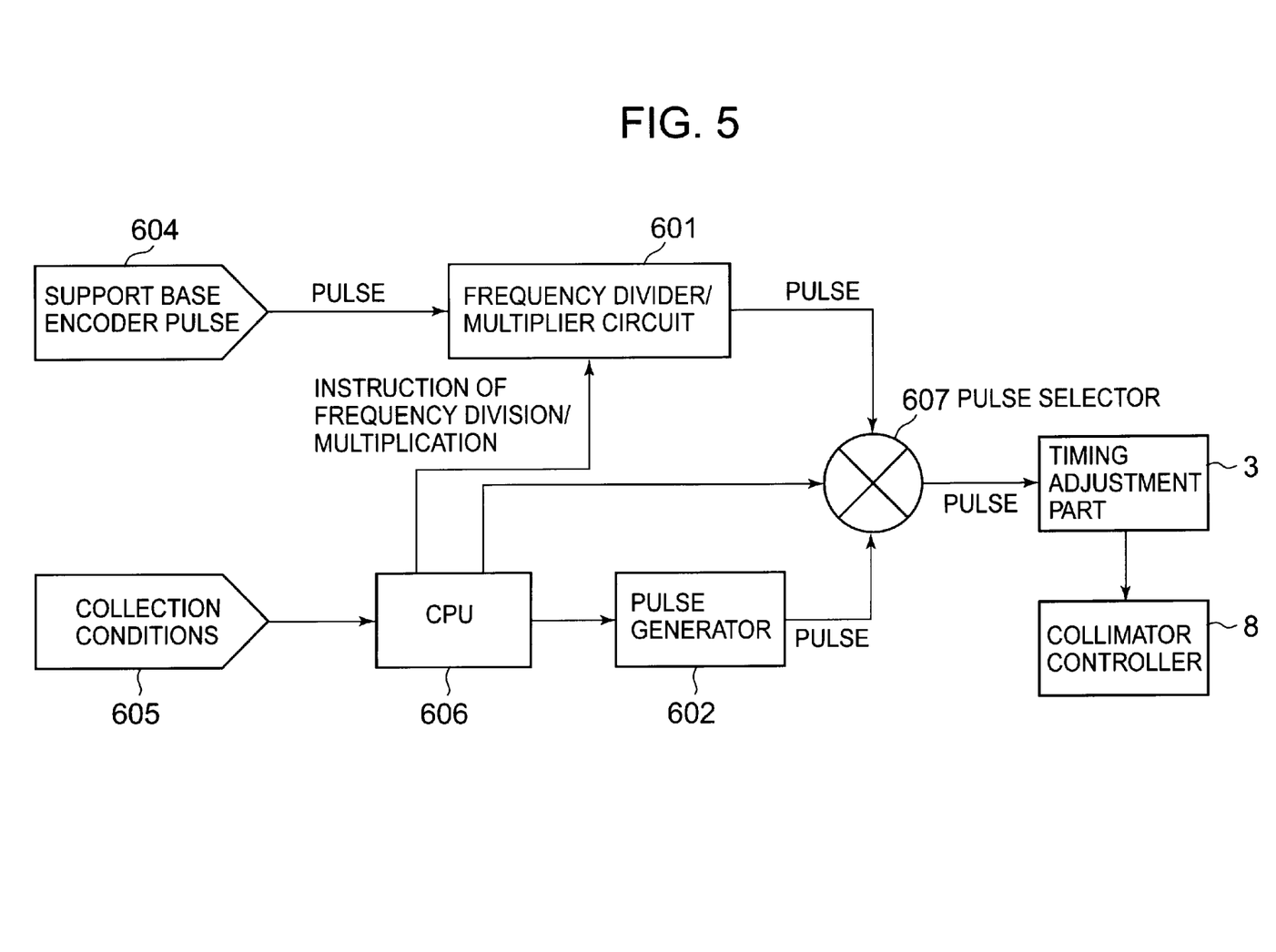
FIG. 5 is a diagram of a synchronous circuit for controlling a collimator at the time of accelerating the speed of movement of a supporting base.

Furthermore, according to the present embodiment, it is also possible to adjust the timing of the control of the collimator plate 107a by the pulse that is generated by the encoder pulse-generating part 103a. Herein, the control of the collimator plate 107a at the time of accelerating the speed of movement of the bed 103 by using either the support base encoder pulse or the timing pulse generated by the pulse generator, is described with reference to FIG. 5. FIG. 5 is a synchronous circuit for controlling a collimator at the time of accelerating the speed of movement of the support base.

A CPU 606 constituting a mounting base control part 111 receives collection conditions 605 from the operation console 104. The CPU 606 instructs a pulse generator 602 to generate a timing pulse. Furthermore, a frequency divider/multiplier circuit 601 receives a support base encoder pulse from the encoder pulse-generating part 103a. The CPU 606 instructs the frequency divider/multiplier circuit 601 to adjust the cycle to be the same as the timing pulse that is generated by the pulse generator 602.

The pulse generator 602 sends the generated timing pulse to a pulse selector 607.

On receipt of the instruction, the frequency divider/multiplier circuit 601 divides or multiples the frequency of the support base encoder pulse to adjust the cycle with the timing pulse that is generated by the pulse generator. Furthermore, the frequency divider/multiplier circuit 601 sends, to the pulse selector 607, the support base encoder pulse that was subjected to the frequency division/multiplication.

After receiving a selection instruction of the pulse to be used for the adjustment of the drive of the collimator plate 107a on receipt of the instruction from the CPU 606, the pulse selector 607 sends, to the timing adjustment part 1, either the support base encoder pulse or the timing pulse generated by the pulse generator 602.

As described above, if there is a difference that exceeds a permissible value in the pulse cycle between the timing pulse generated by a pulse generator and the support base encoder pulse, the synchronization of the operation of the imaging part 3 as well as the collimator plate 107a and the operation of the bed 103 is insufficient. If the synchronization of the operation is insufficient, the reliability of an image that has been imaged then becomes dubious. Therefore, by issuing a warning in the case of a difference that exceeds a permissible value in the pulse cycle between the timing pulse generated by a pulse generator and a support base encoder pulse, re-imaging is possible for diagnosis without using an image with low reliability. Thereby, it becomes possible to eliminate diagnoses with X-ray images having low reliability, and the risk of misdiagnosis may thus be reduced.

As the pulse used for driving the motor of the collimator, a pulse with the frequency divided (or multiplied) may be entered from the support base encoder pulse 604 to the driver circuit, thereby enabling the blade of the collimator to move accordingly even if the bed cannot move at a constant speed because of load variation.

Further, when moving the collimator during accelerating/decelerating the bed, a pulse with the frequency divided (or multiplied) may be entered from the support base encoder pulse 604 to the motor driver, thereby enabling opening/closing with the blade accelerated/decelerated.

Moreover, in the first and second embodiments, the control of the collimator plate 107a located on the bed 103 in the X-ray CT apparatus according to the present invention has been described. However, the X-ray CT apparatus according to the present invention may also be constituted so as to allow a selection of a mode in which an active collimator is used and a mode in which the active collimator is not used by changing the control mode of the collimator plate 107a.

Operations are described of the X-ray CT apparatus in a case of having a constitution that allows the mode selection.

In the case of performing helical scanning by using an active collimator, the operator selects a mode in which the active collimator is used as a control mode for the collimator plate 107a. In this case, the instruction to select a mode in which the active collimator is used is entered into the CPU 606 as a collection condition 605 as shown in FIG. 5. The CPU 606 sends, to the pulse selector 607 or the collimator drive part 107b, the instruction of the active collimator control according to the position of the bed 103 that has been stated in the first and second embodiments.

On the other hand, in the case of helical scanning without using an active collimator, conventional scanning (a method of imaging by rotating the mounting base 102 only one rotation), or dynamic scanning (a method of imaging the same position by rotating the mounting base 102 at the same position), the operator selects, as a control mode for the collimator plate 107a, a mode in which the active collimator is not used. In this case, an instruction to select a mode in which the active collimator is not used is entered into the CPU 606 as a collection condition 605, and the CPU 606 sends, to the pulse selector 607 or the collimator drive part 107b, the instruction for control that is not according to the position of the bed 103 (the active collimator is not used).

As described above, with a constitution that allows the selection of a mode in which an active collimator is used and a mode in which the active collimator is not used, it also becomes possible to deal with a scanning mode other than helical scanning in which an active collimator is used such as in conventional scanning.

What is claimed is:

1. An X-ray CT apparatus comprising:
    a supporter configured to support a patient, capable of moving along the body axis direction of said patient,
    an imaging part including an X-ray-generator configured to irradiate X-rays while rotating around said body axis and an X-ray-detector configured to detect said X-rays that have permeated said patient,
    a collimator configured to change the irradiation field of said X-ray to be irradiated,
    a scan controller configured to control the movement of said supporter and said imaging part, and
    an image-reconstructer configured to reconstruct image data based on the X-rays that have been detected by said X-ray detector, wherein the X-ray CT apparatus comprises:
a detector configured to detect the amount of movement of said patient by said supporter, and
a collimator controller configured to control so as to change the size of the opening of said collimator based on said amount of movement.

2. The X-ray CT apparatus according to claim 1, wherein said scan controller is configured to perform helical scanning and to control so that the speed of movement of said supporter changes while collecting said X-rays by the helical scanning.

3. The X-ray CT apparatus according to claim 1, wherein said collimator controller is configured to control so as to gradually widen the opening of said collimator at the starting portion of a scanning range by helical scanning.

4. The X-ray CT apparatus according to claim 1, wherein said collimator controller is configured to control so as to gradually narrow the opening of said collimator at the end portion of a scanning range by helical scanning.

5. The X-ray CT apparatus according to claim 1, wherein said collimator controller comprises:
a switching part configured to switch a first mode for controlling the movement of said collimator based on said amount of movement that has been detected by said detector and a second mode for controlling the movement of said collimator without using the amount of movement that has been detected by said detector.

6. The X-ray CT apparatus according to claim 5, wherein said first mode is used during helical scanning in which an active collimator is being used, and said second mode is used during scanning other than helical scanning or during helical scanning in which an active collimator is not being used.

7. The X-ray CT apparatus according to claim 1, wherein said scan controller is configured to control the movement of said supporter by using a timing pulse and said detector is configured to generate an encoder pulse based on said movement amount of said supporter,
further comprising:
a pulse-comparing part configured to compare said timing pulse and said encoder pulse, and to issue a warning if there is a difference that exceeds a prescribed value in the pulse cycle.

* * * * *